(12) United States Patent
Murthy et al.

(10) Patent No.: US 6,453,058 B1
(45) Date of Patent: Sep. 17, 2002

(54) COMPUTER-ASSISTED DIAGNOSIS METHOD USING CORRESPONDENCE CHECKING AND CHANGE DETECTION OF SALIENT FEATURES IN DIGITAL IMAGES

(75) Inventors: Sreerama K. Murthy, New Delhi (IN); Carol L. Novak, Newton, PA (US); Jianzhong Qian, Princeton; Zhenyu Wu, Plainsboro, both of NJ (US)

(73) Assignee: Siemens Corporate Research, Inc., Iselin, NJ (US)

( * ) Notice: Subject to any disclaimer, the term of this patent is extended or adjusted under 35 U.S.C. 154(b) by 0 days.

(21) Appl. No.: 09/326,884

(22) Filed: Jun. 7, 1999

(51) Int. Cl.$^7$ .................................................. G06K 9/00
(52) U.S. Cl. ...................................................... 382/128
(58) Field of Search ............................... 382/128, 130, 382/131, 132, 133, 155, 159, 160, 181, 190, 191, 204, 206, 217, 218, 219, 220, 224, 225, 226, 276, 286; 378/4, 5, 8, 21, 37, 51, 53, 54, 58, 62, 63, 70, 74, 87, 165, 166; 128/915; 600/309, 921; 706/424

(56) References Cited

U.S. PATENT DOCUMENTS

| | | | | |
|---|---|---|---|---|
| 5,133,020 A | * | 7/1992 | Giger et al. ................. | 382/128 |
| 5,579,360 A | * | 11/1996 | Abdel-Mottaleb ........... | 378/37 |
| 5,982,915 A | * | 11/1999 | Doi et al. .................... | 382/130 |
| 6,032,678 A | * | 3/2000 | Rottem ........................ | 600/437 |
| 6,125,194 A | * | 9/2000 | Yeh et al. .................... | 382/132 |
| 6,246,782 B1 | * | 6/2001 | Shapiro et al. .............. | 382/128 |
| 6,282,305 B1 | * | 8/2001 | Huo et al. ................... | 382/128 |

* cited by examiner

Primary Examiner—Andrew W. Johns
Assistant Examiner—Shervin Nakhjavan
(74) Attorney, Agent, or Firm—Donald B. Paschburg

(57) ABSTRACT

A computer assisted diagnosis method using change detection of salient features in a first and a second digital image includes the step of converting the first and the second digital image into a first and a second relational attribute graph, respectively. Each graph comprises nodes and arcs. Each node corresponds to an identified salient feature and associated with information comprising a type and characteristics of the corresponding identified salient feature. The arcs correspond to a topological arrangement of the identified salient features. An optimal inexact structural match is determined between the nodes of the first graph and the nodes of the second graph so as to form matched sets of nodes comprising one node from each graph. A node lacking a determined match is matched with a null node. The characteristics of each of the nodes in a matched set are compared to one another to identify variances among the compared characteristics. A corresponding score is generated for each of the nodes in the matched set based on each of the identified variances. The nodes are identified whose appearances vary more than pre-specified thresholds based on the scores corresponding thereto, as well as the nodes matched with the null nodes. Moreover, the nodes corresponding to salient features which have not changed may be identified.

25 Claims, 5 Drawing Sheets

COMPUTER-ASSISTED DIAGNOSIS METHOD USING CORRESPONDENCE CHECKING AND CHANGE DETECTION OF SALIENT FEATURES IN DIGITAL IMAGES

BACKGROUND

1. Technical Field

The present invention relates generally to computer-assisted diagnosis (CAD) and, in particular, to a CAD method using correspondence checking and change detection of salient features in digital images.

2. Background Description

Computer-assisted diagnosis is an important technology in many different clinical applications. However, one of the more prevalent clinical applications for computer-assisted diagnosis is in the detection of breast cancer in women. According to the American Cancer Society, breast cancer is the most common cancer among women, other than skin cancer. It is the leading cause of death among women aged 40 to 55. There are approximately 179,000 new cases of breast cancer in the United States each year and about 43,500 deaths from the disease.

While there are presently no means for preventing breast cancer, early detection of the disease prolongs life expectancy and decreases the likelihood of the need for a total mastectomy. Accordingly, the American Cancer Society recommends that all women aged 40 and older should have a mammogram every year.

Human reading of x-ray mammograms is seldom done in isolation. For example, diagnostic findings from a mammogram are confirmed often after comparing them with those on another mammogram. Change detection may be attempted between images of the same breast in the same view taken at different times (temporal), or between images of the left and right breasts taken at about the same time (bilateral).

As digital storage of mammograms becomes more widespread, it will become increasingly common to do change detection by automatic means in routine screenings. There is already some work in Computer Aided Diagnosis (CADx) for mammography that attempts to perform change detection, e.g., for the identification of masses. Typically with these methods the images first need to be registered. Registering images refers to the process of identifying the correspondences between pixels of the images. Registration methods used in the context of mammography include lining up breast outlines, estimating the correspondence matrices using a few manually specified correspondence points, and so on. Registration is difficult for mammograms because of the differential displacement of soft tissue and structures between images, local and global changes in the appearance of the breast, subtlety of diagnostic findings, and varying image acquisition parameters such as compression and exposure.

Moreover, humans do not seem to accomplish change detection through pixel by pixel comparisons between images. Rather, they are able to quickly detect salient features in the two images and then compare these features based on their location, size and other visual characteristics, while generally ignoring the remainder of the image.

Accordingly, it would be desirable and highly advantageous to have a computer assisted diagnosis method that avoids the problems associated with pixel-based registration methods.

SUMMARY OF THE INVENTION

The present invention is directed to a CAD method using correspondence checking and change detection of salient features in digital images. Changes are detected directly from feature characteristics without resorting to exact registration or exact matching.

In one aspect of the present invention, a computer assisted diagnosis method for automatically detecting changes of salient features in a first and a second digital image includes the step of converting the first and the second digital image into a first and a second relational attribute graph, respectively. Each graph comprises nodes and arcs. Each node corresponds to an identified salient feature and associated with information comprising a type and characteristics of the corresponding identified salient feature. The arcs correspond to a topological arrangement of the identified salient features. An optimal inexact structural match is determined between the nodes of the first graph and the nodes of the second graph so as to form matched sets of nodes comprising one node from each graph. A node lacking a determined match is matched with a null node. The characteristics of each of the nodes in a matched set are compared to one another to identify variances among the compared characteristics. A corresponding score is generated for each of the nodes in the matched set based on each of the identified variances. The nodes are identified whose appearances vary more than pre-specified thresholds based on the scores corresponding thereto, as well as the nodes matched with the null nodes.

These and other aspects, features and advantages of the present invention will become apparent from the following detailed description of preferred embodiments, which is to be read in connection with the accompanying drawings.

DETAILED DESCRIPTION OF PREFERRED EMBODIMENTS

The present invention is directed to a computer-assisted diagnosis method using correspondence checking and change detection of salient features in digital images. Changes are detected directly from feature characteristics without resorting to exact registration or exact matching.

To facilitate a clear understanding of the present invention, illustrative examples are provided herein which describe the invention in applications directed to the detection of breast cancer (i.e., automatically performing change detection of digital mammograms). However, the invention is not solely limited to applications including digital mammograms. It is to be appreciated that the invention may be used to automatically detect changes in digital images corresponding to any part of the body. Moreover, the present invention is equally applicable to digitized or digitally acquired images.

It is to be understood that the present invention may be implemented in various forms of hardware, software, firmware, special purpose processors, or a combination thereof. Preferably, the present invention is implemented in software as a program tangibly embodied on a program storage device. The program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and microinstruction code. The various processes and functions described herein may either be part of the microinstruction code or part of the program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures are preferably implemented in software, the actual connections between the system components (or the process steps) may differ depending upon the manner in which the present invention is programmed.

Figure 1:
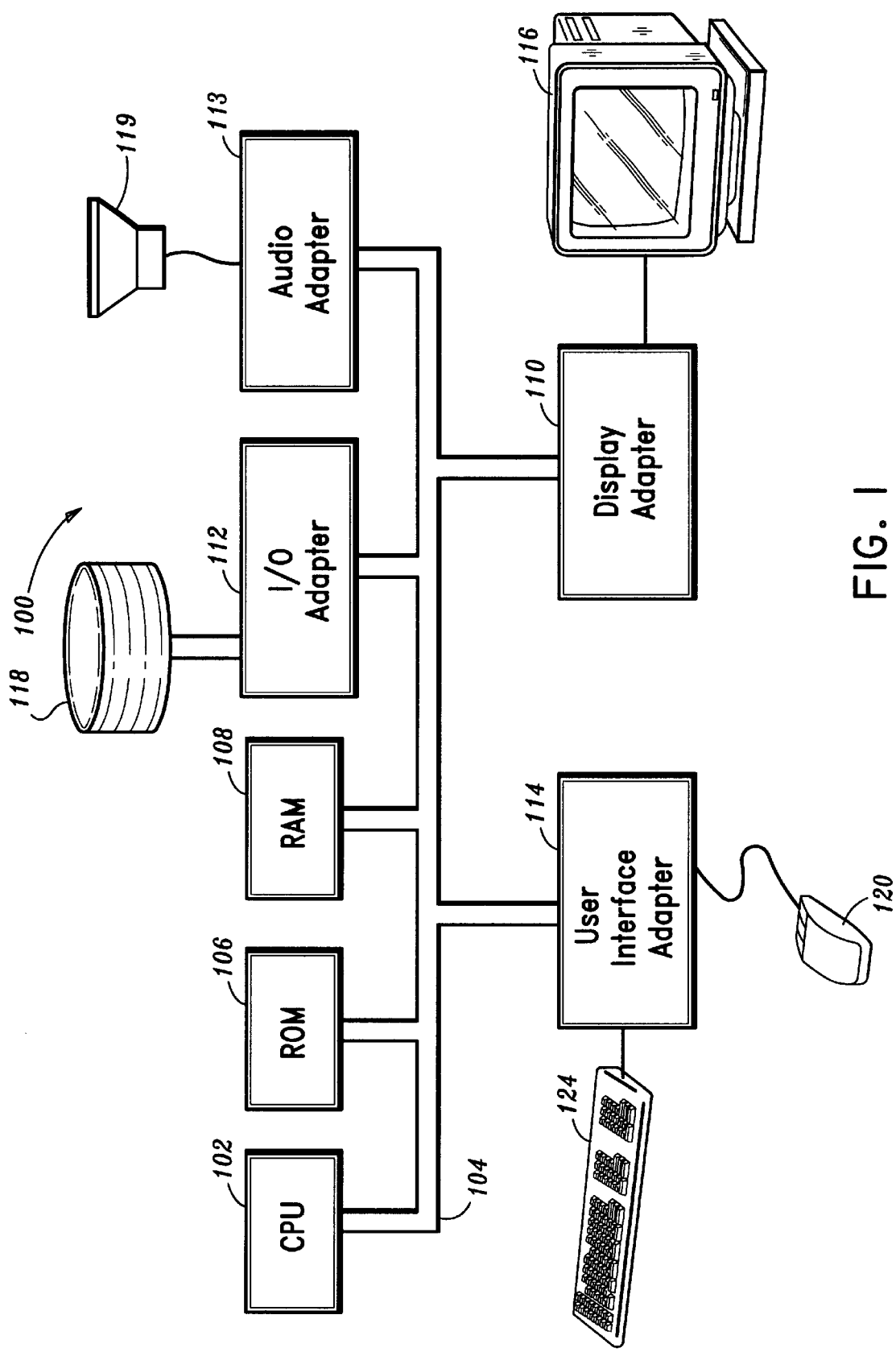
FIG. 1 is a block diagram of a computer processing system to which the present invention may be applied according to an embodiment of the present invention.

FIG. 1 is a block diagram of a computer processing system 100 to which the present invention may be applied according to an embodiment of the present invention. The system 100 includes at least one processor (hereinafter processor) 102 operatively coupled to other components via a system bus 104. A read only memory (ROM) 106, a random access memory (RAM) 108, a display adapter 110, an I/O adapter 112, an audio adapter 113, and a user interface adapter 114 are operatively coupled to system bus 104.

A display device 116 is operatively coupled to system bus 104 by display adapter 110. A disk storage device (e.g., a magnetic or optical disk storage device) 118 is operatively couple to system bus 104 by I/O adapter 112. A speaker 119 is operatively coupled to system bus 104 by audio adapter 113.

A mouse 120 and keyboard 124 are operatively coupled to system bus 104 by user interface adapter 114. The mouse 120 and keyboard 124 are used to input and output information to and from system 100.

A general description of the present invention will now be given to introduce the reader to the concepts and advantages of the invention. Subsequently, more detailed descriptions of various aspects of the invention will be provided.

In general, the invention inputs two digital mammograms in which salient features have been detected. The output of the present invention is a description of, for example, which salient features have remained the same, which features have disappeared or newly appeared, and which features have characteristics (location, size, orientation) that have changed above user-specified thresholds. The changed features, as well as those that have appeared or disappeared, may then be brought to the attention of the user.

Figure 2:
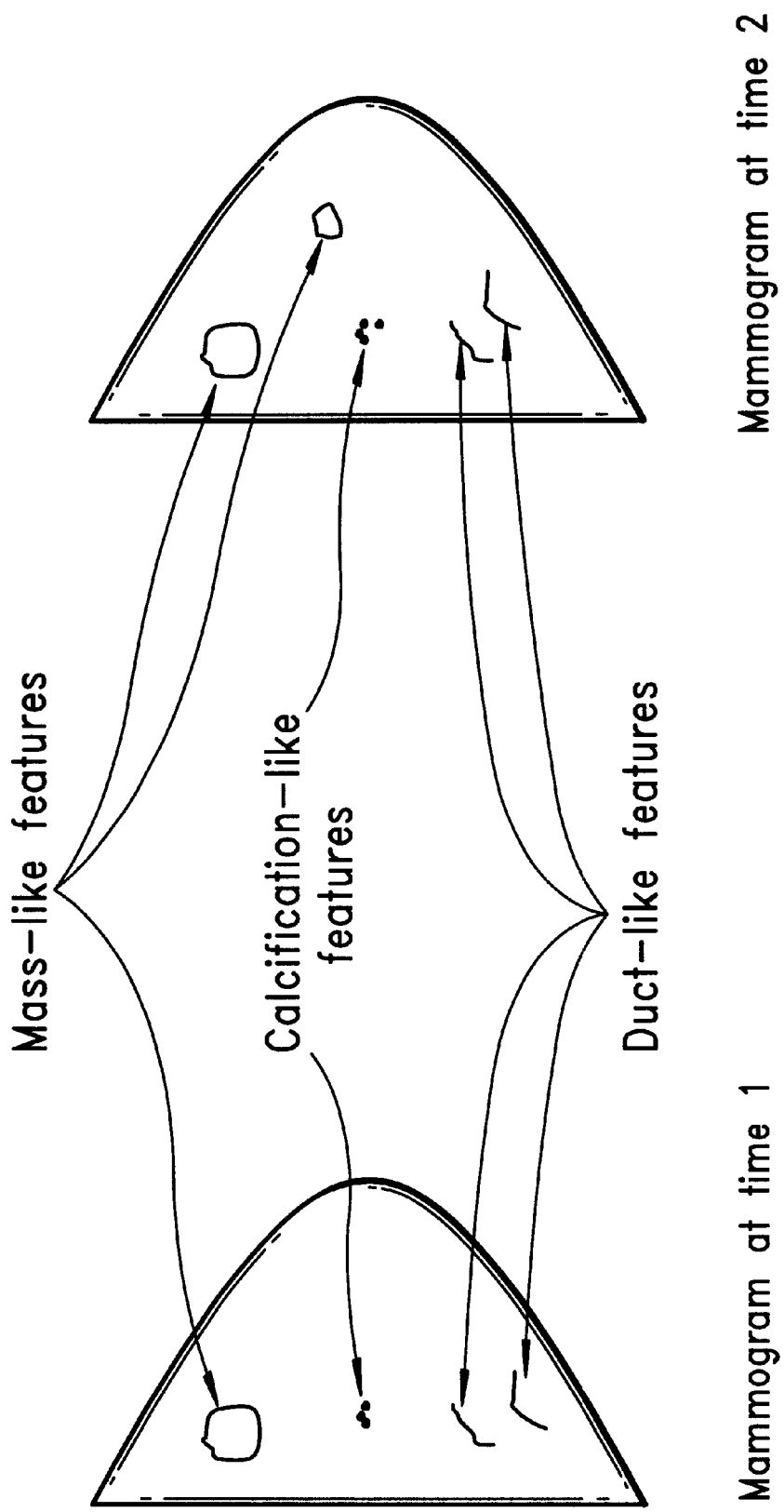
FIG. 2 is a diagram illustrating two hypothetical mammograms to which the present invention may be applied.

FIG. 2 is a diagram illustrating two hypothetical mammograms to which the present invention may be applied. The two mammograms were taken at two different times. This diagram is greatly simplified in showing only a very small number of detected features, in order to illustrate the overall idea of graph building and graph matching as employed in the present invention. In the two mammograms, features considered likely to be masses, features considered likely to correspond to calcifications, and features that may look like ducts are identified.

In providing digital mammograms in which salient features have been identified, a corresponding system and method may be used such as that disclosed in U.S. Ser. No. 09/283,550, entitled "Computer-Assisted Diagnosis Method and System for Automatically Determining Diagnostic Saliency of Digital Images", filed on Apr. 4, 1999, the disclosure of which is incorporated herein by reference.

According to one embodiment of the invention of the Ser. No. 09/283,550 patent application, a CADx method for automatically determining diagnostic saliency of digital images includes the step of providing filters for evaluating the image. Each filter is designed to identify a specific type of diagnostic finding (e.g., well-bounded masses, stellar masses, microcalcifications, skin thickening, architectural distortions, etc.). Further, each filter is associated with the following: a virtual window for defining regions in the image at which the filter is applied; a set of training image patches corresponding to typical appearances of the specific type of diagnostic finding; a distance measure between the training image patches and the regions in the image defined by the virtual window; and a feature set corresponding to the distance measure. The filters are applied to the image to compute distances between the regions in the image defined by the virtual window and the training image patches based on the distance measure and the feature set, for each of the plurality of filters. Regions in the image are ranked as corresponding to a particular type of diagnostic finding based on the computed distances.

The present invention describes how these types of diagnostic findings (salient features) may be used for automatic change detection. However, the method of the present invention is not limited to only features detected by the method and system of the Ser. No. 09/283,550 patent application. It is to be appreciated that the present invention is equally applicable to other types of features, or the same types of features detected through other means.

These salient features may include measures of obvious diagnostic significance, such as the location and characteristics of lesions, calcifications, breast asymmetries, and so forth. Other features that have a high degree of saliency, but which may not necessarily have a straightforward relation to the diagnosis of disease, will also be detected. Examples of such features include breast landmarks such as the outline of the breast, the position of the nipple, and prominent ducts. Other salient features may include lower-level image characteristics such as edges, textures, and primal sketches.

In detecting changes, the present invention translates each digital mammogram into a relational attribute graph. Each such graph contains one node for each salient feature detected in the image. The node encapsulates information such as the type and characteristics of the feature. The arcs contain information about the topology of arrangement of the salient features.

Figure 3:
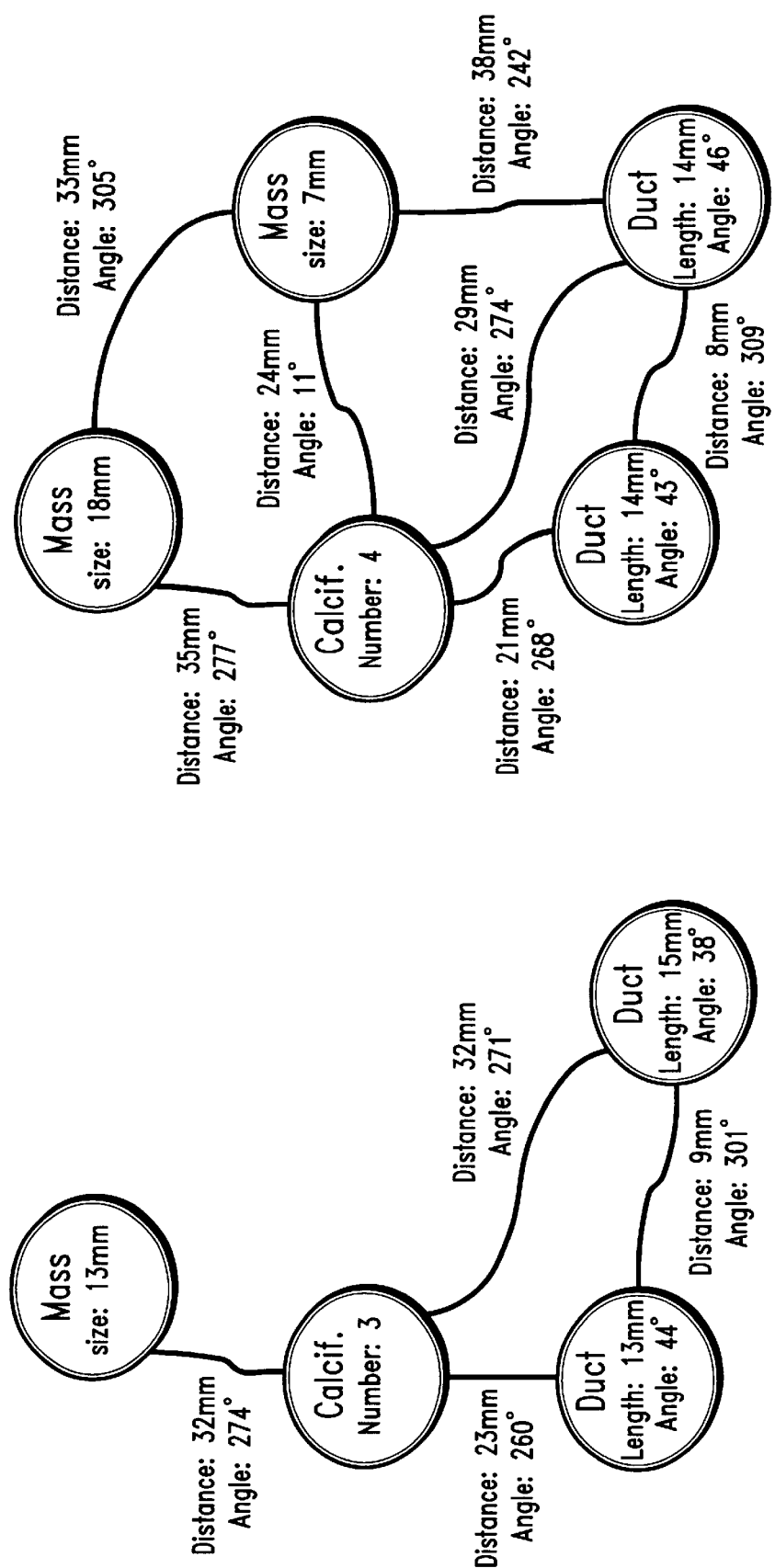
FIG. 3 is a diagram illustrating graphs that can be built from the detected features of the two mammograms of FIG. 2.

FIG. 3 is a diagram illustrating graphs that can be built from the detected features of the two mammograms of FIG. 2. For clarity of illustration, we will presume that graph nodes corresponding to mass-like areas are characterized merely by their size. However, it is to be appreciated that other characteristics such as, for example, mean density, shape, and so forth may also be included.

In this simplified graph example, calcification nodes are characterized solely by the number of small, very bright regions detected in an area. However, it is to be appreciated that additional characteristics such as, for example, the distribution of these calcifications may also be included.

Moreover, in the graph example, duct-like areas are characterized by their length and by the angle between their starting and ending points. However, it is to be appreciated that the node information may include more detailed information, such as, for example, duct curvature.

Lastly, in the graph example, the arcs between the nodes encapsulate the relative positioning of the detected areas by indicating the distance between their centers and the orientation angle between their centers.

Figure 4:
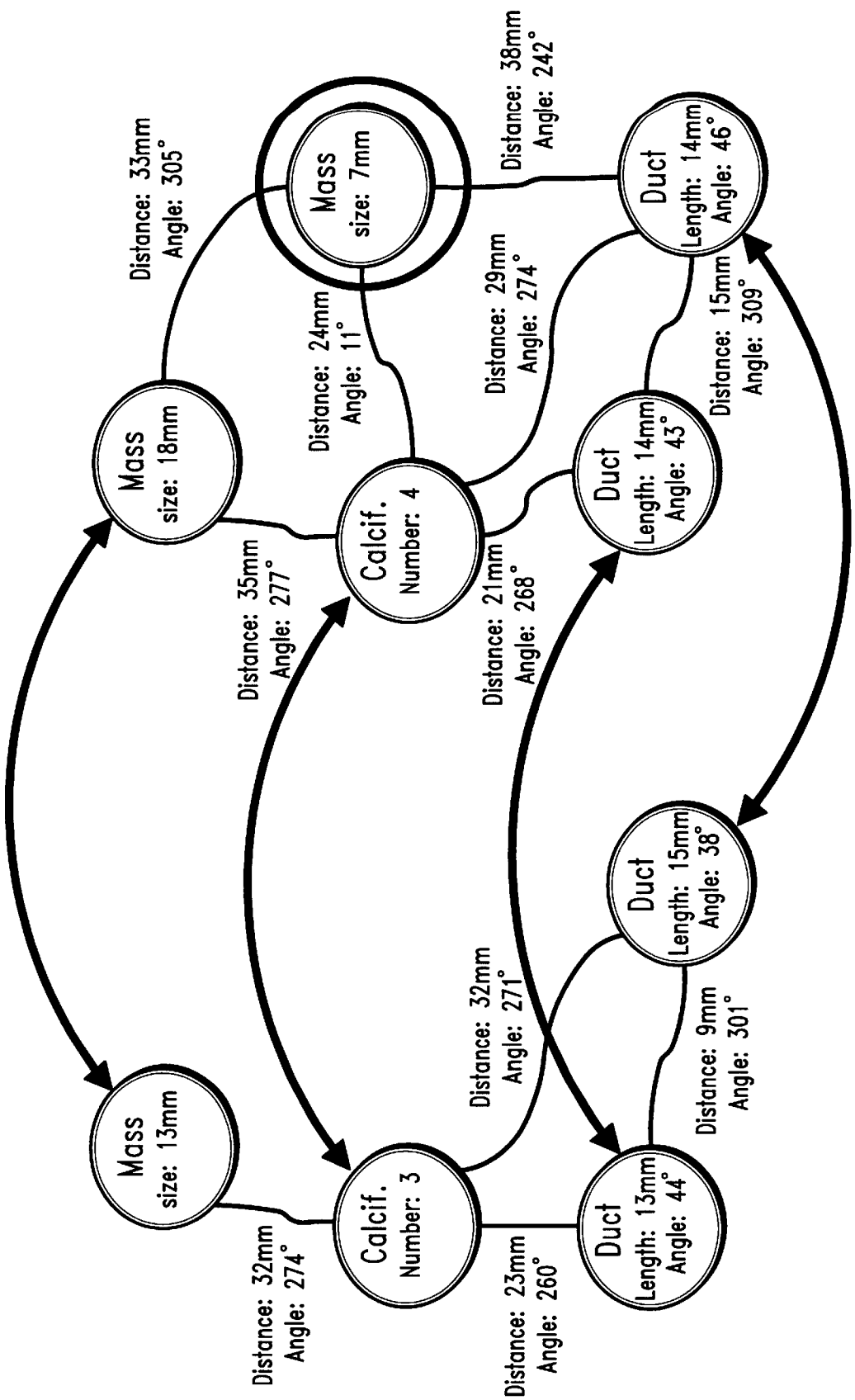
FIG. 4 is a diagram illustrating an inexact match between the two graphs of FIG. 3.

FIG. 4 is a diagram illustrating an inexact match between the two graphs of FIG. 3. Nodes that are matched to each other are indicated by thick arrows. However, it is important to note that the overall graphs are matched to each other, and not just the individual nodes. For example the duct on the right in graph 1 (length=15 mm, angle=38°) more closely matches the duct on the left in graph 2 (length=14 mm, angle=43°) than it does the duct on the right in graph 2 (length=14 mm, angle=46°). However, when considering the overall topological relationships of these nodes to the other nodes, it is clear that the best graph match is the one indicated by the arrows.

Graph matching is used to provide an overall match between two sets of features, rather than just matches between individual features. The other features and the topological relationships between them provide supporting information that is not in the individual features. This is particularly important for two reasons. First, there may be many similar features and thus many possible good matches when the features are considered in isolation. This is the case for the two ducts shown in the figures, since they are quite similar to each other in size and orientation. Without the overall graph structure surrounding them, it would be easy to match the wrong ones. Second, features may change over time to such a degree that taken by themselves they would not be recognized as corresponding to the same feature. For example, the two matched masses (13 mm in graph 1 and 18 mm in graph 2) at the top are sufficiently different in size that, by themselves, they might not be matched. However, it is clear from their similar positioning relative to the other nodes that they could correspond to the same feature which has changed size. Such changes in size may be due to differences in the imaging conditions, but more significantly, could be caused by a disease-related process (i.e. tumor growth).

Once the graphs are matched, significant differences between pairs of matched nodes are brought to the attention of the user. The paired mass feature at the top would be specifically highlighted if a 5 mm growth in size is considered significant. Similarly, the two calcification features that are paired may warrant attention if an increase in the number from three to four is considered clinically significant. The thresholds for attention may be set by physicians according to current clinical practice. Moreover, the thresholds can be adaptively trained by known artificial intelligence (AI) methods.

The small changes in the duct sizes and orientations most likely would not be called out for attention, as these features tend not to have diagnostic significance. However, they are highly useful for generating the graph matches since they provide topological constraints on the other features.

FIG. 4 also shows a circled node corresponding to a mass that was detected in the second mammogram, but where no corresponding node was detected in the first mammogram. One of the key reasons for using inexact graph matching is to handle such occurrences. Sometimes a missing node will occur when a feature is below the saliency threshold set by the detection algorithm. More significantly, a missing node could correspond to a mass or other clinically important feature that has appeared in the breast in the time interval between the two mammograms. A newly appearing feature, particularly when its size is significant, is highly suspicious and warrants attention.

The relative geometric displacement of the detected features, encapsulated by the arcs between them, also differs somewhat between the two graphs. This is to be expected, as compression of the breast during the mammographic examination causes features to be displaced relative to each other. Another benefit of inexact graph matching is that it can handle these kinds of changes and still recognize the optimal global match between the two graphs.

It is to be appreciated that, in simple cases, finding node-to-node correspondence may be done in a pairwise fashion. Given a node in one image, its correspondence can be found by searching within a prespecified window for the best matching node in another image. As the number of nodes, their topological complexity and image distortion/noise increase, such a pairwise approach is often insufficient, because neighborhood relationships between nodes are not used. In contrast, inexact graph matching is capable of taking into account all available information about the nodes and the relationships between nodes (described by attributes of the links between nodes) to produce a globally optimal correspondence list for all nodes. For an article discussing graph matching, see "A Graph Distance Measure for Image Analysis", Eshera et al., IEEE Trans. Syst., Man, Cybern., Vol. SMC-14, pp. 398–408, May/June 1984.

Figure 5:
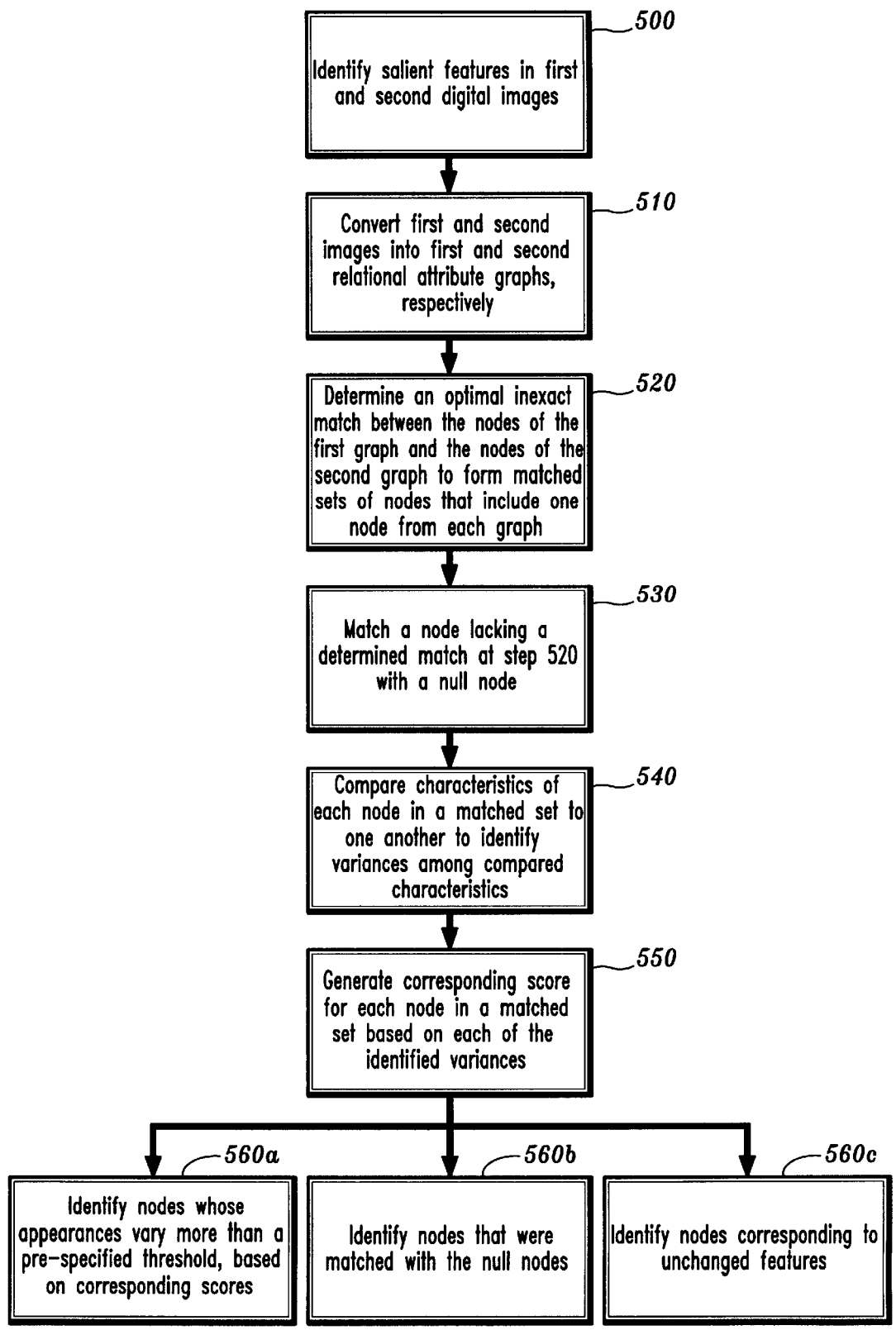
FIG. 5 is a block diagram of a computer-assisted diagnosis (CAD) method for automatically detecting changes of salient features in two digital images according to an embodiment of the present invention.

FIG. 5 is a block diagram of a computer-assisted diagnosis (CAD) method for automatically detecting changes of salient features in a first and a second digital image according to an embodiment of the present invention.

Initially, salient features are identified (detected) in the first and the second digital image (step 500). This a-may be done using the method described in the Ser. No. 09/283,550 patent application or by other automatic means. It is to be appreciated that, irrespective of the feature identifying means used, an increase in the sensitivity at which features are identified results in a corresponding increase in the number of features available for graph matching as described below. It is to be further appreciated that an increase in the number of features, while giving rise to a more precise match, results in a greater computational cost.

The first and the second digital image are converted into a first and a second relational attribute graph, respectively (step 510). The method used for performing the conversion is not critical to the invention and, thus, any methodology may be used. However, each resultant graph should include nodes and arcs. Each node corresponds to an identified salient feature. Further, each node is associated with information comprising the type (e.g., masses, microcalcifications) and characteristics of the corresponding identified salient feature. The arcs correspond to a topological arrangement of the identified salient features. Since only salient features form the nodes of the graphs, regions of the image that are not diagnostically salient have no influence on the checking of corresponding features.

It is to be appreciated that the characteristics associated with a node are represented by quantitative measurements of various physical traits of the feature corresponding to the node. Thus, characteristics of a mass could include the size, shape, mean density, and variation in density of the mass. Characteristics of a calcification could include the total number of clusters corresponding to the calcification, the number of clusters that fall into each of the typical calcification shapes (round, oval, cupped, etc.), the mean density of the calcification, and moment parameters describing the cluster shape.

Inexact structural graph matching is then performed to form matched sets of nodes comprising one node from each graph (step 520). A node lacking a determined match at step 520 is matched with a null node (step 530). The null node is introduced into the lacking graph, i.e., the graph that does not have a node that matches a node in the other graph.

In forming matched sets of nodes, the graph matching step includes global and local correspondence checking. As used herein, the phrase "global correspondence" corresponds to the match between two overall graphs, while the phrase "local correspondence" refers to the match between two individual nodes. Accordingly, global correspondence checking is used to determine the best match between two graphs, while local correspondence checking is used to determine the best match between two nodes. It is to be appreciated that global correspondence checking may incorporate, to some extent, local correspondence checking.

In one embodiment of the present invention, the inexact graph matching step involves finding optimally matched subgraphs from the input graphs 1 and 2. A subgraph in graph 1 is said to match a subgraph in graph 2 if the following conditions are satisfied: (a) for each node in subgraph 1, there exists one and only one corresponding node in subgraph 2; (b) each pair of corresponding nodes must satisfy a pre-specified node similarity criterion (e.g., having an identical feature type); (c) for each arc connecting two nodes in subgraph 1, there exists one and only one corresponding arc in subgraph 2 connecting two nodes in subgraph 2 that correspond to the two nodes in subgraph 1; and (d) each pair of corresponding arcs must satisfy a prespecified arc similarity criterion (e.g., having similar distances and orientations).

Weights may be assigned to each pair of corresponding nodes and arcs in the subgraphs and a match score of a subgraph is then computed as the sum of all the node and arc weights. The inexact graph matching algorithm seeks to find the matched subgraph with the highest match score. According to one embodiment of the invention, the largest matched subgraph may be found in the case when the node and arc weights are set to 1 and 0, respectively.

While the inexact structural graph matching step has been described above with respect to a specific embodiment, it is to be appreciated that such step may be performed using any number of existing methods for accomplishing the same. Preferably, in whichever method is ultimately employed, the arcs corresponding to the topological arrangement of the identified salient features are used in determining the optimal inexact structural match between each of the nodes of the first graph and each of the nodes of the second graph.

The characteristics of each of the nodes in a matched set are compared to one another to identify variances among the compared characteristics (step 540). The methodology used for comparing characteristics of each of the nodes in a matched set is not critical to the invention and, thus, any methodology for accomplishing the same may be used.

The following example, directed to masses, describes but one way in which such comparison may be performed. For a node corresponding to a mass, the measurements associated with it may be represented by x1, x2, . . . , xN, where N is the number of measurements recorded for mass nodes. The node from the other graph to which it is matched has measurements y1, y2, . . . , yN. When the two nodes are compared, the distance between then is given as:

$$\mathrm{sqrt}(a1(x1-y1)^2+a2(x2-y2)^2+\ldots+aN(xN-yN)^2))$$ The weights a1 through aN capture the relative importance of the various mass features in computing the distance.

A similar distance measurement would be used for the other types of nodes. The above distance measure is a weighted Euclidean distance. However, it is to be appreciated that the comparison step is not limited solely to the use of Euclidean distance measures and, thus other types of distance measures may be used by those skilled in the art while maintaining the spirit and scope of the present invention.

A corresponding score is generated for each of the nodes in the matched set based on each of the identified variances (step 550). The scores may be preceded or followed by an identifier which indicates the specific variance (e.g., size, shape, etc.) corresponding to the score.

The nodes whose appearances vary more than pre-specified thresholds, as based on their corresponding scores, are identified (step 560a). Further, the nodes that were matched with the null nodes and, thus, correspond to newly appearing or disappearing features, are identified (step 560b). If so desired, the nodes corresponding to features which have not changed may also be identified (step 560c). Such identification may be performed, for example, visually and/or audibly.

With respect to visual identifications, different color schemes may be used to highlight nodes having a certain trait (e.g., varying appearance, newly appearing, unchanging) on display device 116. Alternatively or concurrently, nodes and their corresponding trait (e.g., varying appearance, newly appearing, unchanging) may be identified via speaker 119.

According to another embodiment of the system, regions of the mammograms being compared are progressively "shuttered", as is commonly done in manual mammogram reading. In "shuttering", only the parts of the corresponding mammograms are compared at a given time. One approach is to build graphs corresponding to only the top 10% of the pixels in each mammogram, and then build subsequent graphs for the second 10%, the third 10%, and so forth. Salient features are extracted globally but compared locally, only within the shuttered regions. This makes the correspondence checking problem simpler as fewer features need to be matched at a time.

It is to be appreciated that directly comparing features between mammograms offers the advantage of improving the specificity of CADx by giving unchanged features little weight in reporting. Features that are determined to be unchanged between mammograms taken at different times, or features that appear in both the left and right breast are usually interpreted by physicians as meriting lesser concern. By automatically computing the correspondences between temporal or bilateral mammogram pairs, the method of the present invention allows the use of highly sensitive feature detectors without the cost of a higher false alarm rate. Further, as inexact graph matching is robust to scale, rotation and translation changes, the change detection method of the present invention inherits this robustness.

Although the illustrative embodiments have been described herein with reference to the accompanying drawings, it is to be understood that the present system and method is not limited to those precise embodiments, and that various other changes and modifications may be affected therein by one skilled in the art without departing from the scope or spirit of the invention. All such changes and modifications are intended to be included within the scope of the invention as defined by the appended claims.

What is claimed is:

1. A computer assisted diagnosis method using change detection of salient features in a first and a second digital image, comprising the steps of:

converting the first and the second digital image into a first and a second relational attribute graph, respectively, wherein each graph comprises nodes and arcs, each node corresponding to an identified salient feature and associated with information comprising a type and characteristics of the corresponding identified salient feature, and the arcs corresponding to a topological arrangement of the identified salient features;

determining an optimal inexact structural match between the nodes of the first graph and the nodes of the second graph so as to form matched sets of nodes comprising one node from each graph, wherein a node lacking a determined match is matched with a null node;

comparing the characteristics of each of the nodes in a matched set to one another to identify variances among the compared characteristics and generating a corresponding score for each of the nodes in the matched set based on each of the identified variances; and reporting as having changed the nodes whose appearances vary more than pre-specified thresholds based on the scores corresponding thereto and the nodes matched with the null nodes.

2. The method according to claim 1, further comprising the step of identifying the salient features in the first and the second digital image.

3. The method according to claim 1, wherein the characteristics corresponding to masses comprise at least one of size and shape.

4. The method according to claim 1, wherein the characteristics corresponding to microcalcifications comprise at least one of a number of calcifications and cluster shapes.

5. The method according to claim 1, wherein said determining step comprises the step of matching subgraphs of the first graph with subgraphs of the second graph.

6. The method according to claim 1, wherein said determining step employs the arcs corresponding to the topological arrangement of the identified salient features in determining the optimal inexact structural match between the nodes of the first graph and the nodes of the second graph.

7. The method according to claim 1, wherein said comparing step is performed with respect to pre-sized regions of the relational attribute graphs.

8. The method according to claim 1, wherein said comparing step compares the characteristics using a distance measure.

9. The method according to claim 1, wherein the characteristics of a particular node correspond to quantitative measurements of at least one physical attribute of the feature corresponding to the particular node, and said comparing step comprises the step of calculating distances between corresponding quantitative measurements of the nodes in the matched sets.

10. The method according to claim 1, wherein the nodes matched with the null nodes correspond to one of newly appearing and disappearing salient features.

11. The method according to claim 1, wherein said identifying step further comprising the step of identifying the nodes corresponding to salient features which have not changed.

12. The method according to claim 1, wherein said identifying step comprises providing at least one of an audio indication and a visual indication of the identified nodes.

13. A program storage device readable by machine, tangibly embodying a program of instructions executable by the machine to perform steps for computer-assisted diagnosis using change detection of salient features in a first and a second digital image, said method steps comprising:

converting the first and the second digital image into a first and a second relational attribute graph, respectively, wherein each graph comprises nodes and arcs, each node corresponding to an identified salient feature and associated with information comprising a type and characteristics of the corresponding identified salient feature, and the arcs corresponding to a topological arrangement of the identified salient features;

determining an optimal inexact structural match between the nodes of the first graph and the nodes of the second graph so as to form matched sets of nodes comprising one node from each graph;

comparing the characteristics of each of the nodes in a matched set to one another to identify variances among the compared characteristics and generating a corresponding score for each of the nodes in the matched set based on each of the identified variances; and reporting as having changed the nodes whose appearances vary more than pre-specified thresholds based on the scores corresponding thereto and the nodes matched with the null nodes.

14. The program storage device according to claim 13, further comprising the step of identifying the salient features in the first and the second digital image.

15. The program storage device according to claim 13, wherein the characteristics corresponding to masses comprise at least one of size and shape.

16. The program storage device according to claim 13, wherein the characteristics corresponding to microcalcifications comprise at least one of a number of calcifications and cluster shapes.

17. The program storage device according to claim 13, wherein said determining step comprises the step of matching subgraphs of the first graph with subgraphs of the second graph.

18. The program storage device according to claim 13, wherein said determining step employs the arcs corresponding to the topological arrangement of the identified salient features in determining the optimal inexact structural match between the nodes of the first graph and the nodes of the second graph.

19. The program storage device according to claim 13, wherein said comparing step is performed with respect to pre-sized regions of the relational attribute graphs.

20. The program storage device according to claim 13, wherein said comparing step compares the characteristics using a distance measure.

21. The program storage device according to claim 13, wherein the characteristics of a particular node correspond to quantitative measurements of at least one physical attribute of the feature corresponding to the particular node, and said comparing step comprises the step of calculating distances between corresponding quantitative measurements of the nodes in the matched sets.

22. The program storage device according to claim 13, wherein the nodes matched with the null nodes correspond to one of newly appearing and disappearing salient features.

23. The program storage device according to claim 13, wherein said identifying step further comprising the step of identifying the nodes corresponding to salient features which have not changed.

24. The program storage device according to claim 13, wherein said identifying step comprises providing at least one of an audio indication and a visual indication of the identified nodes.

25. A computer assisted diagnosis method using change detection of salient features in a first and a second digital image, comprising the steps of:

generating a first and a second relational attribute graph from the first and the second digital image, respectively, wherein each graph comprises nodes and arcs, each node corresponding to an identified salient feature and associated with information comprising a type and characteristics of the corresponding identified salient feature, and the arcs corresponding to a topological arrangement of the identified salient features;

matching the first graph to the second graph so as to form matched sets of nodes comprising one node from each graph;

comparing the characteristics of each of the nodes in a matched set to one another to identify variances among the compared characteristics;

generating a score for each of the nodes in the matched set based on each of the identified variances; and reporting as having changed the nodes whose appearances vary more than pre-specified thresholds based on the scores corresponding thereto.

* * * * *